United States Patent [19]

Ushikubo et al.

[11] Patent Number: 5,449,792

[45] Date of Patent: Sep. 12, 1995

[54] METHOD FOR THE PRODUCTION OF MALEIC ANHYDRIDE

[75] Inventors: Takashi Ushikubo, Yokohama; Kazunori Oshima, Machida, both of Japan

[73] Assignee: Mitsubishi Chemical Corporation, Tokyo, Japan

[21] Appl. No.: 376,654

[22] Filed: Jan. 20, 1995

Related U.S. Application Data

[63] Continuation of Ser. No. 187,489, Jan. 28, 1994, abandoned.

[30] Foreign Application Priority Data

Feb. 4, 1993 [JP] Japan ................... 5-017560

[51] Int. Cl.$^6$ ............... C07D 307/36; C07D 307/34
[52] U.S. Cl. ........................... 549/262; 549/258
[58] Field of Search ........................... 549/262, 258

[56] References Cited

U.S. PATENT DOCUMENTS

| | | | |
|---|---|---|---|
| 4,006,168 | 2/1977 | Kerr | 260/346.8 |
| 4,052,418 | 10/1977 | Suresh et al. | 260/346.74 |
| 4,081,460 | 3/1978 | Kerr et al. | 260/346.75 |
| 4,957,894 | 9/1990 | Haddad et al. | 549/262 |
| 4,966,990 | 10/1990 | Otake et al. | 560/214 |
| 5,049,692 | 9/1991 | Hatano et al. | 558/319 |
| 5,155,235 | 10/1992 | Takashi et al. | 549/262 |
| 5,157,130 | 10/1992 | Sugawara et al. | 549/262 |
| 5,231,214 | 7/1993 | Ushikubo et al. | 558/319 |
| 5,262,548 | 11/1993 | Barone | 549/262 |
| 5,281,745 | 1/1994 | Ushikubo et al. | 558/319 |

OTHER PUBLICATIONS

English Abstract of Japanese Patent JP-A51143615, Oct. 12, 1976.

*Primary Examiner*—Cecilia Tsang
*Attorney, Agent, or Firm*—Oblon, Spivak, McClelland, Maier & Neustadt

[57] ABSTRACT

A method for the production of maleic anhydride in which a hydrocarbon of 4 to 6 carbon atoms is subjected to a vapor phase catalytic oxidation reaction in the presence of a metal oxide catalyst, characterized in that the metal oxide catalyst includes a metal oxide containing Mo, V, Te and X (X representing one or more elements selected from the group consisting of Nb, Ta, W, Ti, Al, Zr, Cr, Mn, Fe, Ru, Co, Rh, Ni, Pd, Pt, Sb, Bi, B, In, P and Ce) as constituent elements thereof, and the proportion of Mo to the total metal elements in the metal oxide is 0.25 or greater in terms of the atomic ratio, and the atomic ratio of each of the other constituent elements V, Te and X with respect to Mo is in the range of 0.01–1.0.

According to the method, the object maleic anhydride may be produced at a high yield using a hydrocarbon of 4 to 6 carbon atoms, particularly n-butane, as the starting material.

7 Claims, No Drawings

METHOD FOR THE PRODUCTION OF MALEIC ANHYDRIDE

This application is a Continuation of application Ser. No. 08/187,489, filed on Jan. 28, 1994, now abandoned.

FIELD OF THE INVENTION

The present invention relates to a method for the production of maleic anhydride by the partial oxidation of a hydrocarbon. Maleic anhydride has industrial importance as an intermediate material for synthetic resins, plasticizers and various other chemical products.

DESCRIPTION OF THE PRIOR ART

As a method for the production of maleic anhydride there has been known in the past a common method in which benzene, butadiene, butene or the like is catalytically reacted with oxygen in the vapor phase at a high temperature, in the presence of a catalyst, but in recent years a method has been developed which employs more economical n-butane as the starting material, and in particular increased interest has been focused on the development of catalysts therefor.

As catalysts for the production of maleic anhydride by the gaseous catalytic oxidation reaction of n-butane there are known oxide catalysts consisting mainly of vanadium and phosphorus, and a large number of reports have been published to date regarding the improvement of the properties of and methods for the production of these catalysts.

However, despite the many heretofore published reports, many problems remain such as insufficient yields of the object maleic anhydride, and complicated methods for the production of the catalysts.

SUMMARY OF THE INVENTION

We the present inventors, as a result of much research regarding methods for the production of maleic anhydride using as the starting material a hydrocarbon of 4 to 6 carbon atoms, have discovered that the object maleic anhydride may be produced at a high yield by a vapor phase catalytic oxidation reaction of these hydrocarbons in the presence of a composite metal oxide catalyst comprising molybdenum, vanadium, tellurium and certain other types of metals, and thus the present invention has been completed.

In other words, the gist of the present invention resides in a method for the production of maleic anhydride in which a hydrocarbon of 4 to 6 carbon atoms is subjected to a vapor phase catalytic oxidation reaction in the presence of a metal oxide catalyst, characterized in that the metal oxide catalyst includes a metal oxide containing Mo, V, Te and X (X representing one or more elements selected from the group consisting of Nb, Ta, W, Ti, Al, Zr, Cr, Mn, Fe, Ru, Co, Rh, Ni, Pd, Pt, Sb, Bi, B, In, P and Ce) as constituent elements thereof, and the proportion of Mo to the total metal elements in the metal oxide is 0.25 or greater in terms of the atomic ratio, and the atomic ratio of each of the above mentioned constituent elements V, Te and X with respect to Mo is in the range of 0.01–1.0.

A more detailed explanation of the present invention is provided below.

DETAILED DESCRIPTION OF THE INVENTION

The metal oxide to be used according to the present invention may contain as X any of the above mentioned elements with Nb, Ta, W, Ti and P preferred, and Nb particularly preferred. In addition, the proportion of Mo to the total of all the metal elements in the metal oxide is 0.25 or greater in terms of the atomic ratio, and the atomic ratios of the other constituent elements mentioned above with respect to Mo are, within the above mentioned ratio, particularly preferred to be in the range of 0.1–0.6 for V, 0.05–0.4 for Te and 0.01–0.6 for X. Here, the atomic ratio of X is the ratio of the total atomic number of all the elements encompassed by X. Furthermore, the resident proportion of the total of Mo, V, Te and X making up the total metal elements in the metal oxide is 0.75 or greater, and preferably 1, in terms of the atomic ratio; that is, the metal elements in the metal oxide consist solely of Mo, V, Te and X. If P is used as an element in X, then the atomic ratio with respect to V is 0.5 or less, and preferably 0.01–0.3.

Furthermore, the metal oxide is preferably one which has a specific crystal structure. In concrete terms, the pattern of the X-ray diffraction peaks of the metal oxide (using Cu-K$\alpha$ rays as the X-ray source) at a specific angle of diffraction $2\theta$ reveals the five major diffraction peaks shown below.

| Diffractions angle $2\theta$ ($\pm 0.3°$) | X-ray grating face Median interval | Relative strength |
| --- | --- | --- |
| 22.1 | 4.02 | 100 |
| 28.2 | 3.16 | 20–150 |
| 36.2 | 2.48 | 5–60 |
| 45.2 | 2.00 | 2–40 |
| 50.0 | 1.82 | 2–40 |

There is some variation in the X-ray diffraction peak strengths depending on the measuring conditions of each of the crystals, but the relative strengths are in the above ranges if the peak strength at $2\theta 22.1°$ is defined as 100. Also, the peak strengths at $2\theta 22.1°$ and 28.2° appear most intensely.

The method of preparing the above mentioned metal oxide is as follows. For example, for the preparation of the metal oxide $Mo_aV_bTe_cNb_xO_n$ using Nb as element X, an aqueous solution of telluric acid, an aqueous solution of ammonium niobium oxalate and an aqueous solution or slurry of ammonium para-molybdenate are successively added to an aqueous solution containing a prescribed amount of ammonium metavanadate in amounts so that the atomic ratio of each of the metal elements is a prescribed proportion, the mixture is dried by evaporation to dryness, spray drying, lyophilization, vacuum drying, etc., and finally the remaining dry matter is calcined, normally at 350°–700° C. and preferably at 400°–650° C. normally for 0.5–30 hours, and preferably for 1–10 hours, to obtain the object metal oxide.

The calcination method is not particularly limited, and it may be carried out in ambient air as is common, but to obtain a catalyst having the above mentioned specific X-ray diffraction peak pattern, it is preferable that the calcination environment be substantially free of oxygen. In concrete terms, the calcination is preferably carried out in an inert environment of nitrogen, argon, helium or the like, and preferably in vacuo.

The starting materials for the above mentioned metal oxide are not particularly limited to the ones described above, and a wide range of ones may be used including, for example, oxides such as $MoO_3$, $V_2O_5$, $V_2O_3$, $TeO_2$, $Nb_2O_5$, etc., halides or oxyhalides such as $MoCl_5$, $VCl_4$, $VOCl_3$, $NbCl_5$, etc., and alkoxides and organic metal compounds such as $Mo(OC_2H_5)_5$, $Nb(OC_2H_5)_5$, $VO(OC_2H_5)_3$, molybdenum acetylacetonate, etc.

A metal oxide obtained in this manner may be used alone as a solid catalyst, but it may also be used in combination with a well-known carrier such as, for example, silica, alumina, titania, aluminosilicate, diatomaceous earth and zirconia.

The method according to the present invention is one for the production of maleic anhydride by subjecting a hydrocarbon of 4 to 6 carbon atoms to a vapor phase catalytic reaction in the presence of a catalyst containing the metal oxide described above.

According to the present invention, a hydrocarbon of 4 to 6 carbon atoms may be used as the starting material, but more preferable for use are straight chain C4 hydrocarbons, including those substituted with alkyl or other hydrocarbon groups, and specific examples thereof include n-butane, 1-butene, cis-2-butene, trans-2-butene, 1,3-butadiene, and their hydrocarbon-substituted forms, as well as mixtures thereof. Most preferred for use is n-butane.

The details of the mechanism of the oxidation reaction according to the present invention is not clear, but it proceeds with either the oxygen atoms present in the above mentioned metal oxide or the molecular oxygen present in the feed gas. If the feed gas is to contain molecular oxygen, then the molecular oxygen may be pure oxygen gas, but since no particular purity is required, it is usually more economical to use an oxygen-containing gas such as air. The feed gas to be used is normally a gas mixture containing a hydrocarbon such as n-butane and an oxygen-containing gas, but the hydrocarbon such as n-butane and the oxygen-containing gas may be supplied alternately.

Furthermore, the hydrocarbon such as n-butane may be subjected to the vapor phase catalytic reaction alone as the feed gas substantially in the absence of molecular oxygen. Preferably, in such a case, a method wherein a portion of the catalyst is appropriately drawn out from the reaction zone and fed to an oxidative regenerator, and after regeneration the catalyst is re-fed into the reaction zone. The method for the regeneration of the catalyst may be one in which, for example, an oxidizing gas such as oxygen, air, nitrogen monoxide or the like is caused to flow through the catalyst in the regenerator, usually at 300°–600° C.

Below there is provided a more detailed explanation regarding the present invention in the case in which n-butane is used as the hydrocarbon and air as the oxygen source. The reactor system to be used may be a fixed bed, fluidized bed, etc., but since the reaction is exothermic, the reaction temperature may be easily controlled for a fluidized bed system. The proportion of the air to be supplied for the reaction is important in view of its selectivity for the resulting maleic anhydride, and air usually exhibits a high selectivity for maleic anhydride in a range of 0.1–50 moles, and particularly 0.2–30 moles per mole of n-butane. The reaction is usually conducted under atmospheric pressure, but it may also be conducted under a slightly increased or under reduced pressure. If another hydrocarbon is used as the starting material, the composition of the feed gas may be selected based on the conditions for n-butane.

In the method according to the present invention, the reaction temperature is normally 300°–480° C. and preferably about 350°–450° C. Also, the gas space velocity SV for the vapor phase reaction is normally in a range of 100–10,000 $hr^{-1}$, and preferably 300–2,000 $hr^{-1}$. As the diluent gas for adjustment of the space velocity and partial oxygen pressure may be used an inert gas such as nitrogen, argon or helium.

EXAMPLES

A more detailed explanation of a concrete embodiment of the present invention is provided below with reference to the Examples, but it should be understood that the present invention is by no means restricted to such specific Examples.

In the following Examples, the conversion (%), selectivity (%) and yield (%) are determined by the following formulas. Conversion of n-butane (%)=(moles of n-butane consumed/moles of n-butane supplied)×100 Selectivity for maleic anhydride (%)=(moles of maleic anhydride produced/moles of n-butane consumed)×100 Yield of maleic anhydride (%)=(moles of maleic anhydride produced/moles of n-butane supplied)×100

Examples 1-9

A complex metal oxide having an empirical formula 90 wt % $Mo_1V_{0.3}Te_{0.23}Nb_{0.12}O_n$+10 wt % $SiO_2$ was prepared in the following manner. In 325 ml of hot water was dissolved 15.7 g of ammonium metavanadate, and to this solution were successively added 23.6 g of telluric acid and 78.9 g of ammonium paramolybdenate, to prepare a uniform aqueous solution. Also, 56.5 g of an aqueous silica sol solution containing 20 wt % of $SiO_2$ was mixed with 117.5 g of an aqueous solution of ammonium niobium oxalate with a niobium concentration of 0.456 mol/kg, to prepare a slurry. This slurry was heated to remove the water and obtain a solid. The solid was calcined for 2 hours at 600° C. in a nitrogen stream.

Upon measurement of the X-ray powder diffraction (using Cu-Kα rays) of the metal oxide obtained in this manner, major diffraction peaks were found at 22.1° (100), 28.2° (92.0), 36.2° (23.7), 45.1° (14.8), 50.0° (16.0) with a diffraction angle of $2\theta$ (the numbers in parentheses indicate the relative peak strengths with the peak strength of 22.1° defined as 100).

Of the solid catalyst obtained in this manner, 1.18 g was charged into a reactor, and gas was supplied thereto at a molar ratio of n-butane:air=1:24, at the reaction temperatures and space velocities listed in Table 1, for the vapor phase catalytic reaction. The results are shown in Table 1.

TABLE 1

| Example | Space velocity ($hr^{-1}$) | Temperature (°C.) | Conversion of n-butane (%) | Selectivity for maleic anhydride (%) | Yield of maleic anhydride (%) |
| --- | --- | --- | --- | --- | --- |
| 1 | 1000 | 422 | 96.6 | 37.0 | 35.7 |
| 2 | 1000 | 407 | 88.3 | 39.6 | 34.9 |
| 3 | 1000 | 393 | 70.5 | 42.8 | 30.2 |
| 4 | 1000 | 378 | 47.8 | 42.1 | 19.9 |
| 5 | 1000 | 363 | 29.6 | 42.2 | 12.5 |
| 6 | 2000 | 433 | 90.5 | 33.4 | 30.2 |
| 7 | 2000 | 419 | 80.7 | 36.6 | 29.3 |
| 8 | 2000 | 403 | 61.4 | 39.7 | 24.4 |

TABLE 1-continued

| Example | Space velocity (hr$^{-1}$) | Temperature (°C.) | Conversion of n-butane (%) | Selectivity for maleic anhydride (%) | Yield of maleic anhydride (%) |
|---|---|---|---|---|---|
| 9 | 2000 | 390 | 41.7 | 44.1 | 18.4 |

Comparisons 1-3

The solid catalysts listed in Table 2 were obtained without using specific starting materials in the method of preparing catalyst in Example 1.

Of each of the solid catalysts obtained in this manner, 1.18 g was charged into a reactor, and gas was supplied thereto at a molar ratio of n-butane:air=1:24, under the reaction conditions listed in Table 2, at a space velocity of 10,000 hr$^{-1}$ for the vapor phase catalytic reaction. The results are shown in Table 2.

TABLE 2

| Comparative Example | Solid catalyst | Temperature (°C.) | Conversion of n-butane (%) | Yield of maleic anhydride (%) |
|---|---|---|---|---|
| 1 | $Mo_1V_{0.3}Te_{0.23}O_n$ | 420 | 73.4 | 8.6 |
| 2 | $Mo_1V_{0.3}O_n$ | 400 | 79.6 | 8.2 |
| 3 | $Mo_1Te_{0.23}O_n$ | 380 | 0.2 | 0 |

Examples 10-12

The solid catalysts listed in Table 3 were obtained using an additional amount of phosphoric acid as a starting material in the method of preparing the catalyst in Example 1.

Of each of the solid catalysts obtained in this manner, 1.18 g was charged into a reactor, and gas was supplied thereto at a molar ratio of n-butane:air=1:24, under the reaction conditions listed in Table 3, for the vapor phase catalytic reaction. The results are shown in Table 3.

TABLE 3

| Example | Composition of catalyst | Space velocity (hr$^{-1}$) | Reaction temperature (°C.) | Conversion of n-butane (%) | Selectivity for maleic anhydride (%) | Yield of maleic anhydride (%) |
|---|---|---|---|---|---|---|
| 10 | 90 wt %-$Mo_1V_{0.3}Te_{0.23}Nb_{0.12}P_{0.01}O_x$ + 10 wt %-$SiO_2$ | 1510 | 420 | 72.2 | 33.3 | 24.0 |
| 11 | 90 wt %-$Mo_1V_{0.3}Te_{0.23}Nb_{0.12}P_{0.05}O_x$ + 10 wt %-$SiO_2$ | 1520 | 430 | 68.3 | 34.7 | 23.7 |
| 12 | 90 wt %-$Mo_1V_{0.3}Te_{0.23}Nb_{0.12}P_{0.10}O_x$ + 10 wt %-$SiO_2$ | 1000 | 440 | 80.6 | 32.0 | 25.8 |

What is claimed is:

1. A method for the production of maleic anhydride comprising:

subjecting n-butane to vapor phase catalytic oxidation in air at an amount of 0.2-30 mols of air per mole of n-butane in the presence of a metal oxide catalyst, said metal oxide catalyst including a metal oxide containing Mo, V, Te and X, wherein X is at least one element selected from the group consisting of Nb, Ta, W, Ti, Al, Zr, Cr, Mn, Fe, Ru, Co, Rh, Ni, Pd, Pt, Sb, Bi, B, In, P and Ce, as constituent elements thereof, wherein the proportion of Mo to the total metal elements in said metal oxide is 0.25 to 0.8, in terms of the atomic ratio, and the atomic ratios of said other constituent elements V, Te and X with respect to Mo range as 0.1-0.6, 0.05-0.4 and 0.01-0.6 respectively.

2. The method of claim 1, wherein said element X is at least one member selected from the group consisting of Nb, Ta, W and Ti.

3. The method of claim 1, wherein X is Nb.

4. The method of claim 1, wherein X is P.

5. The method of claim 1, wherein the pattern of the X-ray diffraction peaks of the metal oxide (using Cu-K$\alpha$ rays as the X-ray source) at a specific angle of diffraction 2 $\theta$ reveals the five major diffraction peaks as follows:

| X-ray grating face | |
|---|---|
| 22.1° | 100 |
| 28.2° | 20-150 |
| 36.2° | 5-60 |
| 45.2° | 2-40 |
| 50.0° | 2-40 |

6. The method of claim 1, wherein the temperature of the gas phase oxidation reaction ranges from 300° to 480° C.

7. The method of claim 1, wherein the gas space velocity for the reaction is 100-10,000 hr$^{-1}$.

* * * * *